United States Patent
Choi et al.

(10) Patent No.: US 6,852,512 B2
(45) Date of Patent: Feb. 8, 2005

(54) EXPRESSION VECTORS FOR PRODUCTION OF FOREIGN PROTEINS AS SOLUBLE FORMS

(75) Inventors: Seong Il Choi, Taejun (KR); Baik Lin Seong, Taejun (KR)

(73) Assignee: Hanil Synthetic Fiber Co., Ltd. (KR)

( * ) Notice: Subject to any disclaimer, the term of this patent is extended or adjusted under 35 U.S.C. 154(b) by 0 days.

(21) Appl. No.: 09/974,248

(22) Filed: Oct. 9, 2001

(65) Prior Publication Data

US 2002/0137146 A1 Sep. 26, 2002

Related U.S. Application Data

(62) Division of application No. 09/077,868, filed as application No. PCT/KR97/00186 on Oct. 4, 1997, now abandoned.

(30) Foreign Application Priority Data

Oct. 4, 1996 (KR) ............................................. 96-44010

(51) Int. Cl.[7] ........................... C12P 21/06; C12N 9/00; C12N 1/20; C12N 15/00; C07H 21/04
(52) U.S. Cl. ............................... 435/69.1; 435/4; 435/6; 435/183; 435/252.3; 435/320.1; 435/252.8; 530/350; 536/23.2; 536/23.4; 536/23.56; 536/23.74
(58) Field of Search ................................ 435/4, 6, 69.1, 435/183, 252.3, 252.8, 320.1, 412, 252.33, 41, 440, 471, 488, 243; 530/350, 412; 536/23.2, 23.4, 23.5–23.74

(56) References Cited

U.S. PATENT DOCUMENTS 5,801,013 A 9/1998 Tao et al.

5,871,987 A 2/1999 Sassanfar et al.

OTHER PUBLICATIONS

Escalante et al., 1993, J. Biol. Chem, vol. 268(8):6014–6023.*

Brevet et al. J. Biol. Chem., 1995, vol. 270(24):14439–44.*

Commans S et al. solution structure of the anti–codon binding domain of *Escherichia coli* lysyl–tRNA synthetase and studies of its interaction with tRNA. 1995, J. Mol.Biol. vol. 253:100–113.

Clark R. L. et al. Roles of two lysyl–tRNA synthetases of *E.coli*: Analysis of nucleotide sequences and mutant behavior. 1990, J. Bacteriol. vol. 172(6):3237–3243.

Sachdev, et al., 1998, *Biochemical and Biophys. Res. Communications* 244 (No. 3):933–937 "Order of Fusions between Bacterial and Mammalian Proteins Can Determine Solubility in ".

* cited by examiner

*Primary Examiner*—Manjunath N. Rao
(74) *Attorney, Agent, or Firm*—Muserlian, Lucas and Mercanti LLP

(57) ABSTRACT

The present invention relates to novel expression vectors which can produce foreign proteins as soluble forms by using lysyl-tRNA synthetase and a process for preparing foreign proteins by using the expression vectors. Particularly, the present invention relates to the expression vectors which can provide foreign proteins as fused and soluble forms by exploiting the structure and expression pattern of lysyl-tRNA synthetase and the processes for preparing foreign proteins in *E. coli* effectively, which can be utilized industrially to produce active proteins in mass.

9 Claims, 11 Drawing Sheets

EXPRESSION VECTORS FOR PRODUCTION OF FOREIGN PROTEINS AS SOLUBLE FORMS

CROSS REFERENCE TO RELATED APPLICATIONS

This application is a divisional of U.S. application Ser. No. 09/077,868 filed on Jun. 4, 1998 and abandoned on Oct. 23, 2001, incorporated herein by reference which is a 371 of PCT/KR1997/00186 filed Oct. 4, 1997.

FIELD OF THE INVENTION

The present invention relates to novel expression vectors which can produce foreign proteins as soluble forms by using lysyl tRNA synthetase and a process for preparing foreign proteins by using the expression vectors.

More particularly, the present invention relates to the expression vectors which can provide foreign proteins as fused and soluble forms by exploiting the structure and expression pattern of lysyl-tRNA synthetase and the process for preparing foreign proteins in E. coli effectively, which can be utilized industrially to produce active proteins in mass.

BACKGROUND OF THE INVENTION

With the advance of genetic engineering, heterologous proteins which are used industrially as medicine and the like, have been produced by utilizing animal cells, yeasts and prokaryotes such as E. coli. Especially E. coli has been exploited as a popular host cell to produce foreign proteins since it grows fast and has been studied more thoroughly than any other organisms.

Unfortunately, E. coli lacks cellular components necessary for posttranslational modification processes like glycosylation, disulfide-crosslinking or the like. And foreign proteins produced massively and excessively in E. coli are sequestered into inclusion bodies, which can be easily separated. But in order to obtain active proteins, these inclusion bodies should be solubilized to form primary structure by using high concentration of urea, guanidium HCl or the like and then refolded removing the above reagents.

Generally, the refolding process for preparing a active protein can not be always performed successfully since its result varies according to the cases. For example, proteins having high molecular weight, such as antibodies, tissue plasmingen activator, factor VIII and so on, are not refolded easily to become active proteins. And, it is difficult to produce a recombinant protein on a large scale.

Therefore, it is very important to express foreign proteins as soluble forms in E. coli for improving the problems caused in above cases.

Presently, following methods have been exploited to express foreign proteins as soluble forms effectively.

First, there is a method in which N-terminus of foreign protein is linked to signal peptide so as to secrete foreign protein into periplasm of E. coli as a soluble form (Stader, J. A. and Silhavy, T. J., 1970, Methods in Enzymol., 165: 166–187). Since the foreign proteins are not expressed effectively by the process, this method is not useful industrially.

Second, there is a method in which foreign proteins are expressed with chaperone genes such as groES, groEL, dnaK and the like to obtain soluble proteins (Goloubinoff, P., Gatenby, A. A. and Lorimer, G. H., 1989, Nature, 337: 44–47). But this method is not general to prevent the formation of inclusion body since it is available on only specific proteins.

Third, there is a method in which target proteins are fused at the C-terminus with fusion partner proteins which can be expressed highly in E. coli. Since the target proteins are linked at the C-terminus of fusion partners, translation initiation signal of the fusion partner protein can be exploited usefully. And the solubility of the fused foreign protein increases so that large amount of foreign proteins can be obtained as soluble forms in E. coli.

Lac Z or Trp E protein have been utilized as a fusion partner protein in order to produce fusion proteins in E. coli. But active-form proteins can not be obtained easily since most fusion proteins were expressed in the forms of inclusion body. Therefore, many researches have been accomplished to obtain novel fusion partner proteins which facilitates the production of active-form proteins. Practically, some fusion partner proteins have been developed, such as glutathione-S-transferase (Smith, D. B. and Johnson, K. S., 1988, Gene, 67: 31–40), maltose-binding protein (Bedouelle, H. and Duplay, P., 1988, Euro. J. Biochem., 171: 541–549), protein A (Nilsson, B. et al., 1985, Nucleic Acid Res., 13 1151–1162), Z domain of protein A (Nilsson, B. et al., 1987, Prot. Eng., 1: 107–113), protein Z (Nygren, P. A. et al., 1988, J. Mol. Recog, 1: 69–74) and thioredoxin (Lavallie, E. R. et al., 1993, Bio/Technology, 11: 187–193).

Although foreign proteins have been expressed by linking the fusion partner described above and prepared as soluble forms, some were expressed as inclusion body or partly as soluble proteins according to the fusion partner protein.

Particularly, thioredoxin has been known to be the most successful protein as a fusion partner. However, in the case of thioredoxin E. coli transformant should be cultured at low temperature such as 15° C. in order to express most fusion proteins as soluble forms. Since E. coli grows very slowly at that temperature, the process using the thioredoxin may be inefficient.

Lysyl-tRNA synthetase (hereinafter it refers to "Lys RS") and its gene have been investigated as described below, which is preferable for the fusion partner protein and expressed highly in E. coli.

Although in E. coli aminoacylation is performed by using a specific aminoacyl-tRNA synthetase, two lysyl-tRNA synthetases which are encoded from lys S gene and lys U gene are involved in the aminoacylation independently. lys S gene is expressed constitutively in normal condition and lys U gene is induced by heat shock, low pH, anaerobiosis, L-alanine, L-leucine, L-leucyldipeptide. And amino acid sequences derived from the two genes show 88% of homology.

In addition, the X-ray crystallographical structure of lysyl-tRNA synthetase which is expressed from lys U gene (hereinafter it refers to "Lys U") was illucidated at the 2.8 Å resolution level (Onesti, S., Miller. A. D. and Brick, P., 1995, Structure, 3: 163–176). Lys U protein is composed of homodimer which has N-terminal domain contacting with tRNA and C-terminal domain of dimer interface showing the enzyme activity (see FIG. 1).

In addition, nuclear magnetic resonance (NMR) structure of N-terminal domain (31–149 amino acid residues) of lysyl-tRNA synthetase which is expressed from lys S gene (hereinafter it refers to "Lys S") was revealed by Frederic Dardel group (Stephane, C. et al., J. Mol. Biol., 253 100–113). As Lys U protein and Lys S protein share a high degree of identity in the amino acid sequences, the N-terminal structures of the two enzymes are identified to be very similar.

In detail, the N-terminal domain of lysyl-tRNA synthetase has secondary structure of five stranded antiparallel β barrel which is composed of α-helix (H4) located between 3rd and 4th β-sheet and contiguous 3 α-helices. The post-part of N-terminal domain corresponds to OB fold (A1A2A3H4A4A5) which is found in proteins binding with oligosaccharides or oligonucleotides commonly. It has been reported that OB fold was discovered in aspartyl-tRNA synthetase of yeast, β-subunit of heat labile enterotoxin, berotoxin and staphylococcal nuclease (Murzin, A. G., 1993, *EMBO J*, 12: 861–867).

The N-terminal domain of Lys RS protein of which the structure is described above shows the following characteristics as a fusion partner protein.

When the lys S gene was expressed in *E. coil*, the Lys S protein has accumulated to 80% of total soluble proteins. Since the Lys S protein is composed of a homodimer of which the contact region is located at the C terminus of the monomer, the fusion protein using intact Lys S protein, or the C-terminal domain of the Lys S protein as a fusion partner, makes a heterodimer with the Lys S protein of *E. coil*.

But such a heterodimer is fatal to *E. coil*. Thus, the C-terminal domain of Lys S protein is not appropriate as a fusion partner protein, and only the N-terminal domain can be exploited as a fusion partner protein. Practically, only the N-terminal domain of Lys S protein (hereinafter it refers to "Lys N") can be used to express foreign proteins well, to approximately 40% of the total proteins, and produced mostly as a soluble form.

As mentioned above, OB fold located in the N-terminal domain of Lys RS protein has a secondary structure which facilitates protein folding and increases the solubility of fusion proteins expressed.

The present inventors have researched to develop a fusion partner protein which is useful to produce heterologous proteins by recombinant DNA technology. Thus we have demonstrated that the N-terminal domain of lysyl-tRNA synthetase can be utilized as a fusion partner protein to produce foreign proteins massively in a soluble form. And by using the lysyl-tRNA synthetase, we have developed novel *E. coli* expression vectors and a process for preparing active foreign proteins effectively.

SUMMARY OF THE INVENTION

The object of the present invention is to provide expression vectors containing total or part of aminoacyl-tRNA synthetase gene. The aminoacyl-tRNA synthetase gene can be obtained from all kinds of cells.

The expression vectors of the present invention are composed of linker peptide sequence, tag sequence, protease recognition site, restriction enzyme recognition site for inserting foreign gene or the like, in addition to the aminoacyl-tRNA synthetase gene.

In addition, the object of the present invention is to provide the *E. Coli* expression vectors containing total or part of lysyl-tRNA synthetase gene. The lysyl-tRNA synthetase gene can be selected among lys S gene or lys U gene.

Particularly, the present invention provides the expression vector pGE-lysRS containing intact lys S gene.

In addition, the object of the present invention is to provide the expression vectors containing the N-terminal domain gene of lysyl-tRNA synthetase.

The present invention provides the expression vectors containing the N-terminal domain of lysyl-tRNA synthetase which is deleted at the amino acid residues 1 to 13. And the present invention also provides the expression vectors containing the N-terminal domain gene of lysyl-tRNA synthetase which is deleted at the amino acid residues 1 to 29.

In addition, the present invention provides the expression vector containing only OB fold gene of lysyl-tRNA synthetase. For the purpose, the expression vectors contain the N-terminal domain gene of lysyl-tRNA synthetase which is deleted at the amino acid residues 1 to 65.

Particularly, the present invention provides the *E. coli* expression vector pGE-lysN. *E. coli l HMS* 174 strain was transformed by the expression vector pGE-lysN and the transformant has been deposited with Korea Research Institute of Bioscience and Biotechnology, Korea, on Sep. 26, 1997 (accession number: KCTC 0388 BP).

The object of the present invention is to provide a process for preparing useful foreign proteins as soluble forms of fusion protein by inserting the foreign genes into the above expression vectors.

Particularly, the present invention provides the expression vector plysN-GMcsf by inserting GMcsf (human granulocyte and macrophage colony stimulating factor) gene into the expression vector pGE-lysN. Host cell was transformed with the expression vector and induced to express GMcsf protein as a fusion protein.

At that time, all kinds of *E. coli* strain can be used, which is appropriate for the expression of the fusion protein. Preferably, *E. coli* HMS 174 strain can be used as a host cell.

Particularly, the present invention provides the expression vector plysN-Gcsf by inserting Gcsf (human granulocyte colony stimulating factor) gene into the expression vector. By using the above process, Gcsf protein is prepared.

Particularly, the present invention provides the expression vector plysN-TIMP2 by inserting TIMP2 (human tissue inhibitor of metalloprotease 2) gene into the expression vector. By using the above process, TIMP2 protein is prepared.

Stick is helix structure and arrow is β-sheet structure.

Figure 1:
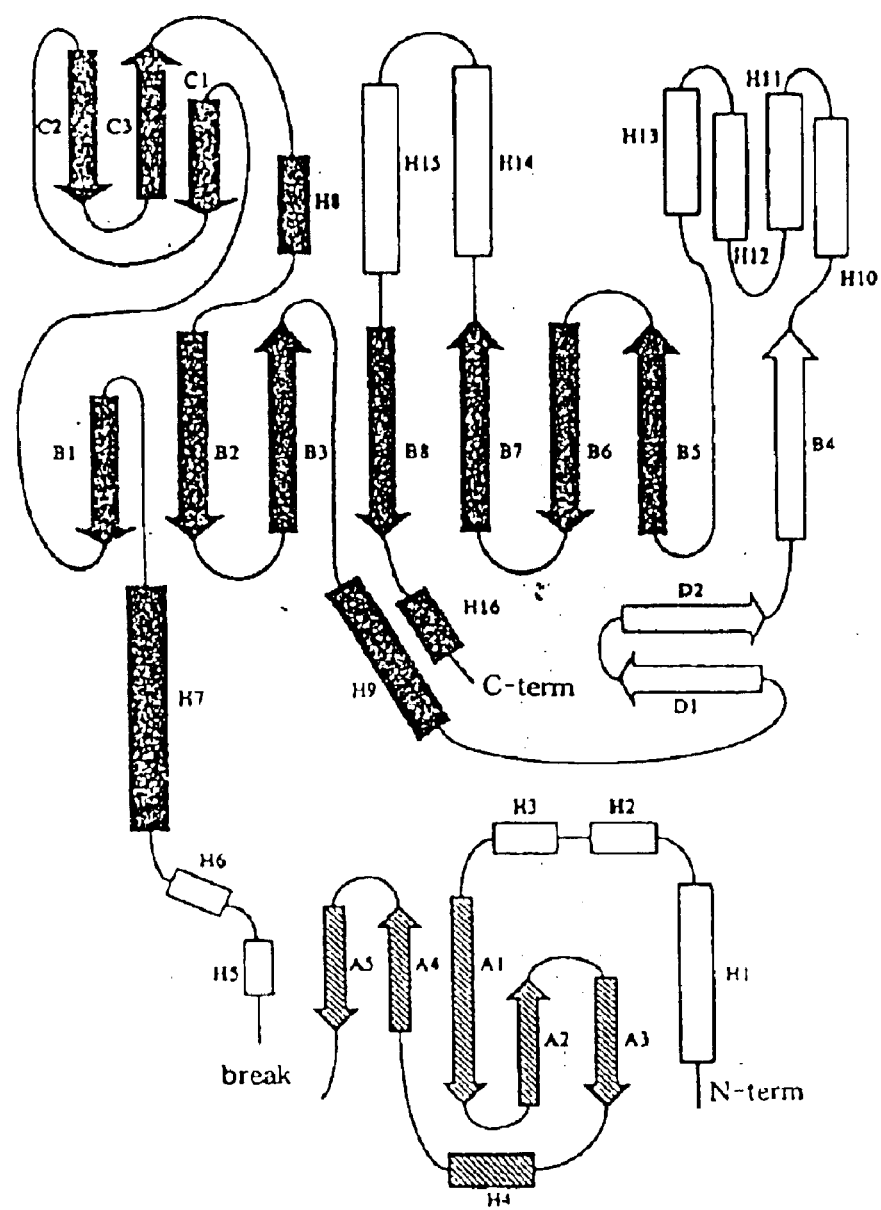
FIG. 1 depicts the secondary structure of lysyl-tRNA synthetase (Lys U).
Figure 2:
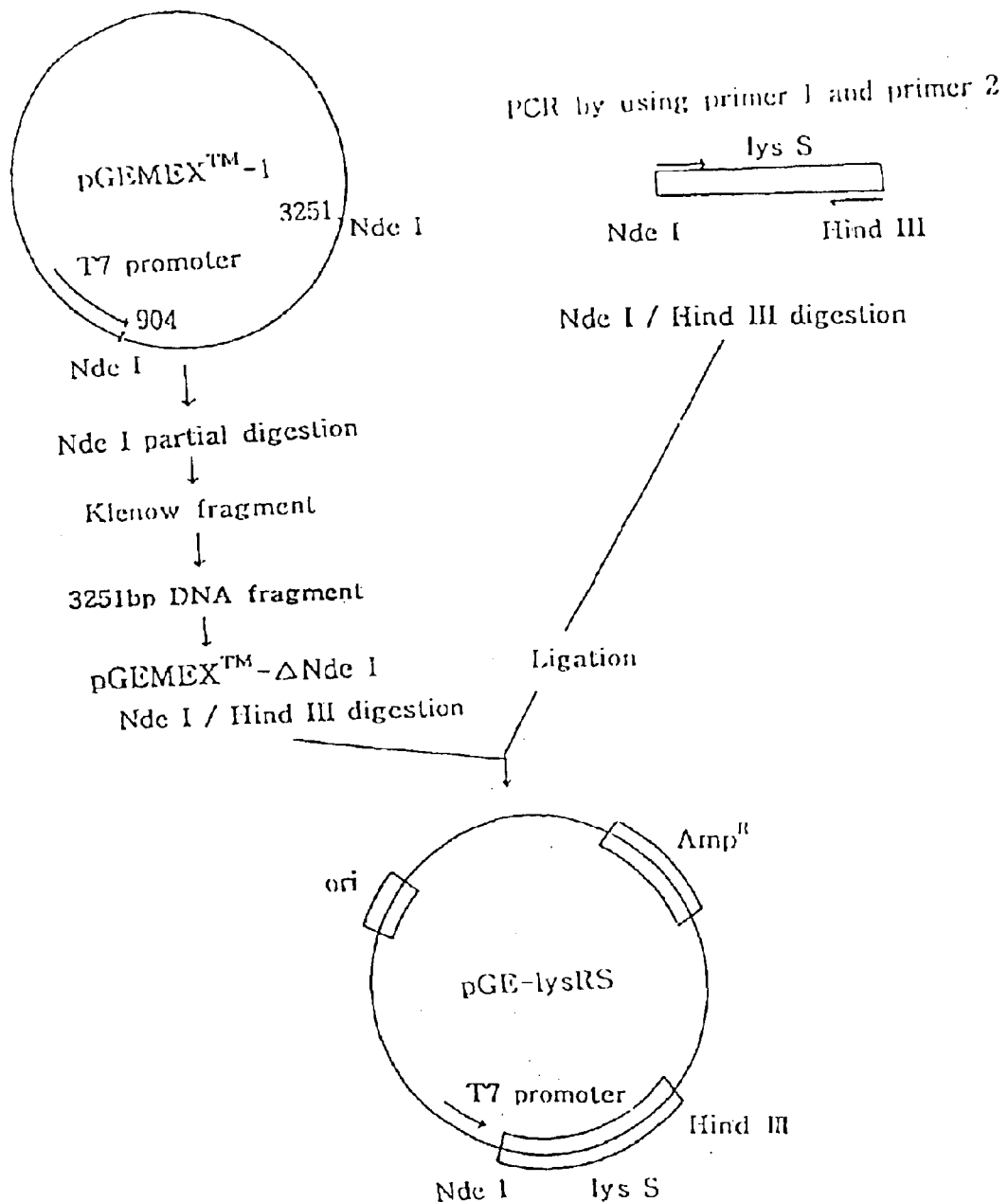

FIG. 2 depicts a strategy for constructing the expression vector pGE-lysRS into which lys S gene is inserted.

Figure 3:
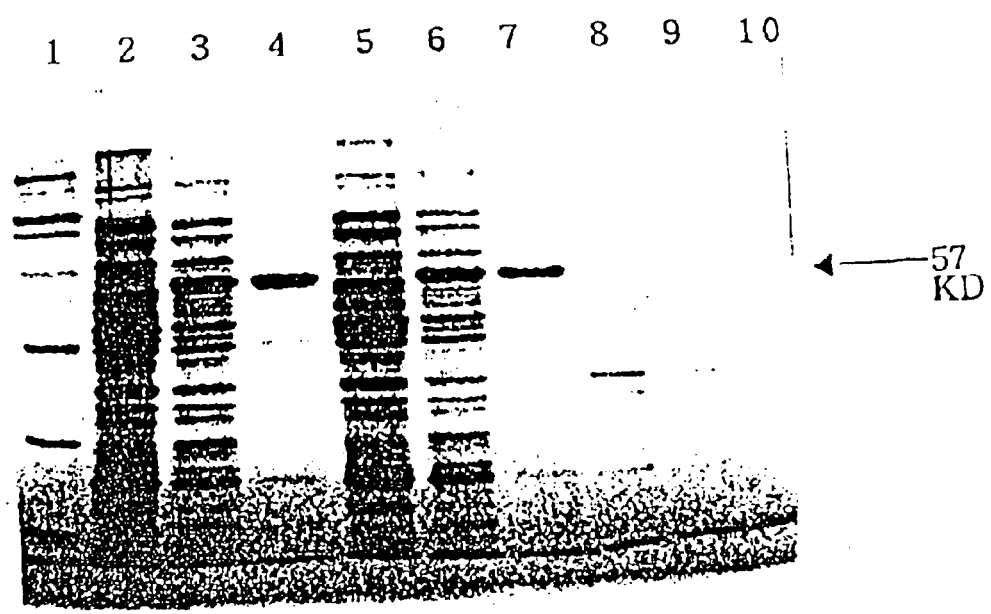
Figure 4:
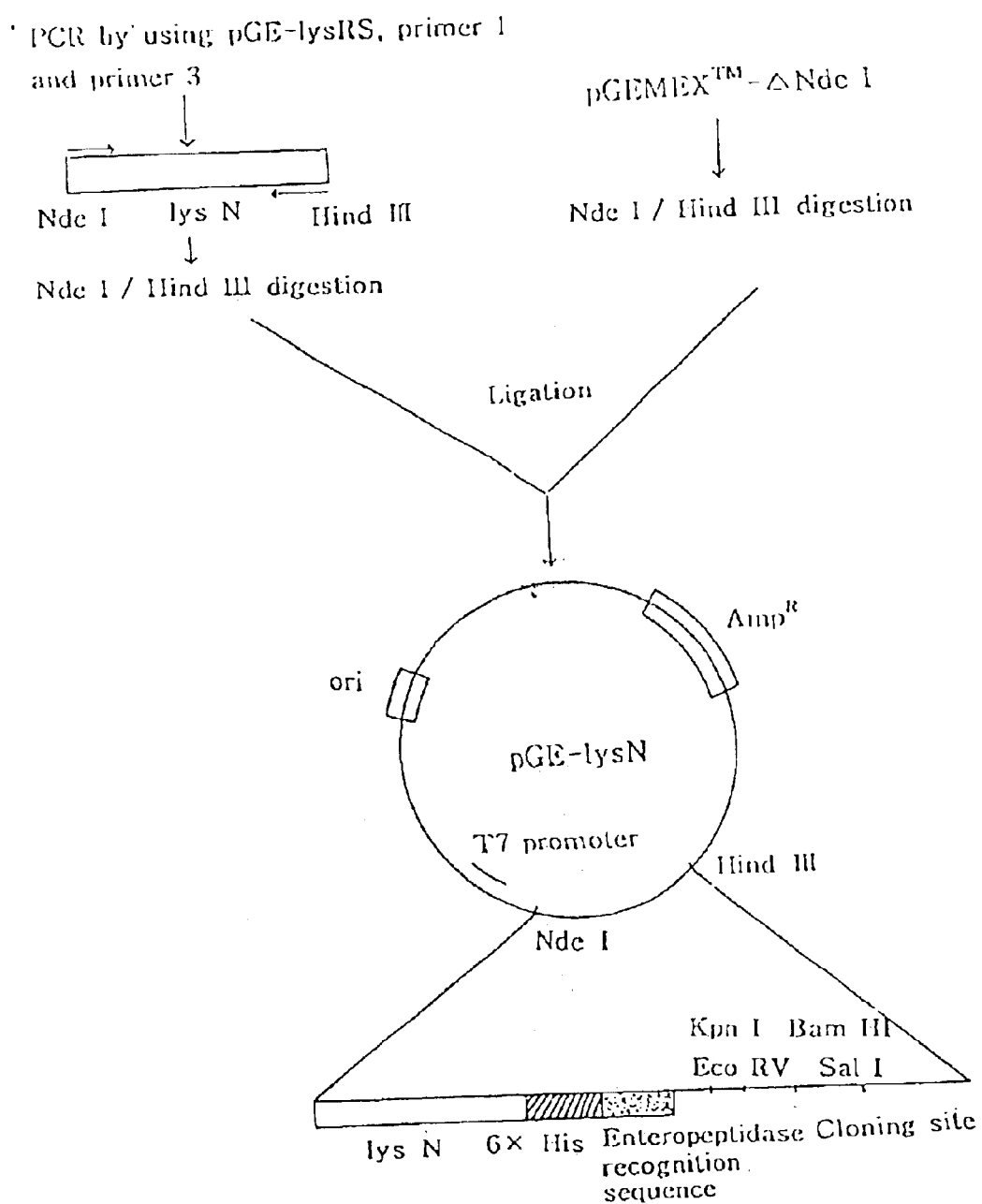

FIG. 3 depicts the expression of Lys S protein by performing SDS-polyacrylamide gel electrophoresis, which used *E. coli l HMS* 174 strain transformed with the expression vector pGE-lysRS of the present invention.

lane 1: standard protein marker;
lane 2: total proteins of *E. coli* induced for the protein expression;
lane 3: total proteins of *E. coli* transformant;
lane 4: total proteins of *E. coli* transformant induced for the protein expression;
lane 5: supernatant of disrupted *E. coli* induced;
lane 6: supernatant of disrupted *E. coli* transformant;
lane 7: supernatant of disrupted *E. coli* transformant induced;
lane 8: precipitate of disrupted *E. coli* induced;
lane 9: precipitate of disrupted *E. coli* transformant;
lane 10: precipitate of disrupted *E. coli* transformant induced FIG. 4 depicts a strategy for constructing the expression vector pGE-lysN which uses the N-terminal domain of Lys S protein as a fusion partner protein.

Figure 5:
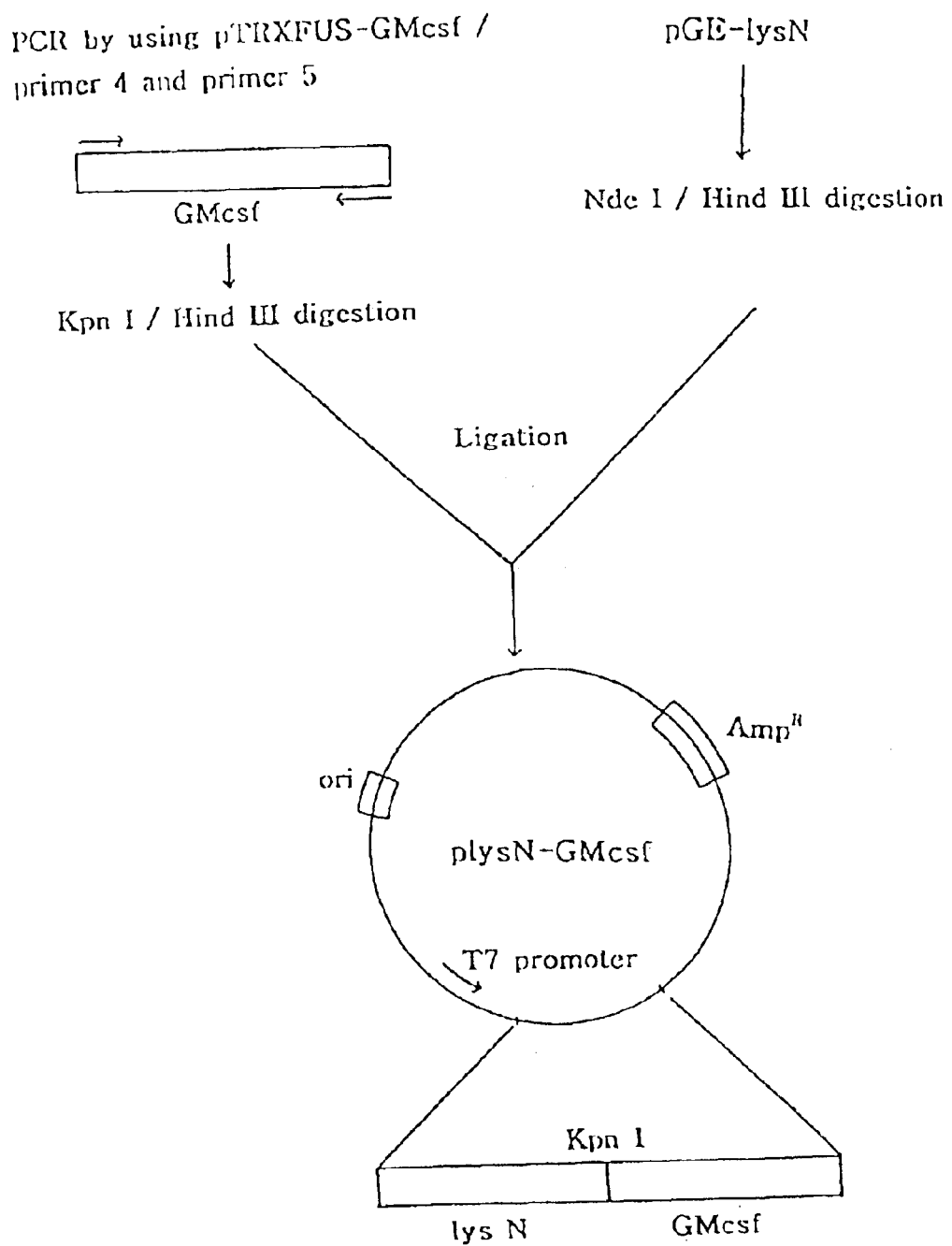

FIG. 5 depicts a strategy for constructing the *E. coli* expression vector pLysN-GMcsf which expresses GMcsf protein by using the expression vector pGE-lysN.

Figure 6:
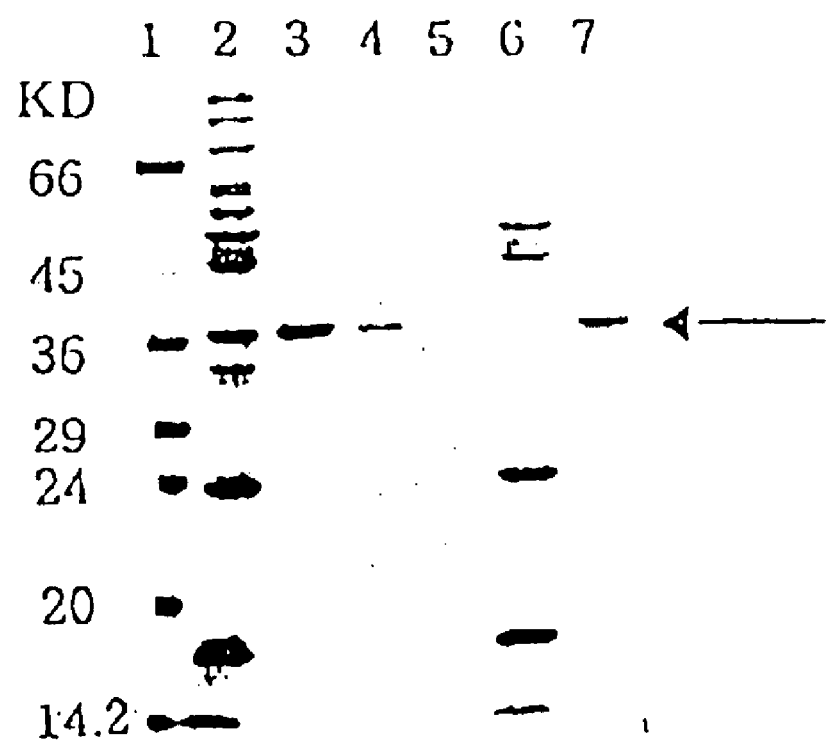
Figure 7:
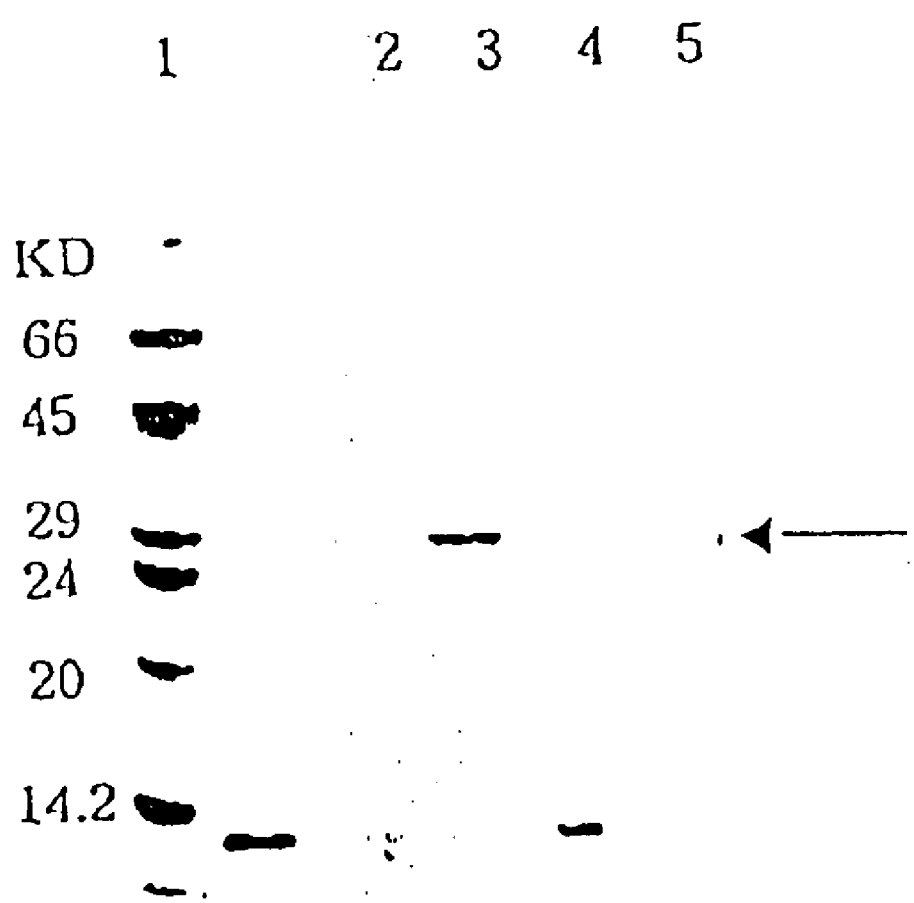
Figure 8:
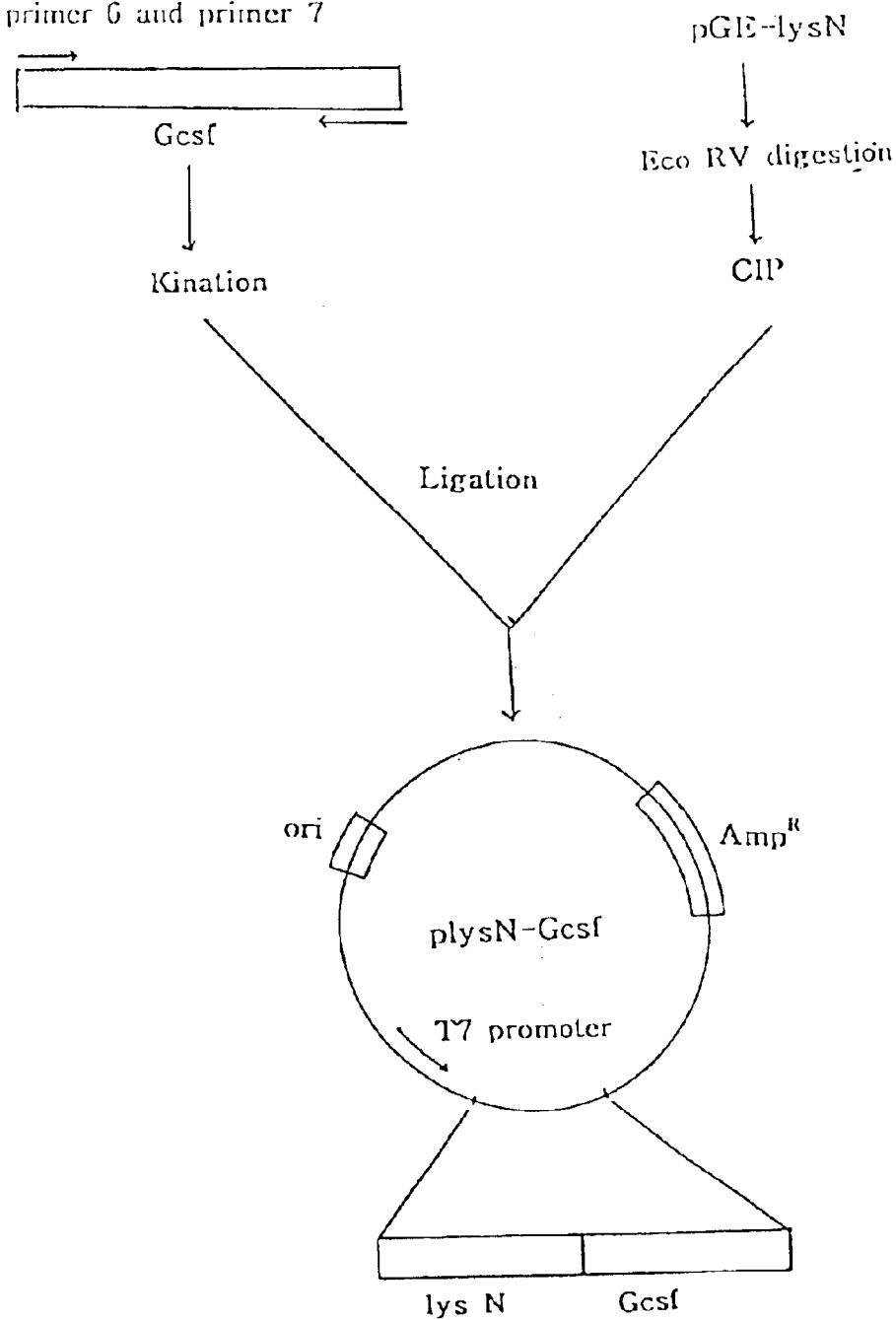

FIG. 6 depicts the expression of GMcsf protein by performing SDS-polyacrylamide gel electrophoresis, which used *E. coli* HMS 174 strain transformed with the expression vector pLysN-GMcsf of the present invention.

lane 1: standard protein marker;
   lane 2: total proteins of *E. coli* transformant;
   lane 3: total proteins of *E. coli* transformant induced for the expression;
   lane 4: precipitate of disrupted *E. coli* transformant;
   lane 5: precipitate of disrupted *E. coli* transformant induced;
   lane 6: supernatant of disrupted *E. coli* transformant;
   lane 7: supernatant of disrupted *E. coli* transformant induced;

FIG. 7 depicts the expression of GMcsf protein for comparison by performing SDS-polyacrylamide gel electrophoresis, which used thioredoxin as a fusion partner protein and *E. coli* GI724 strains transformed with the expression vector pTRXFUS-GMcsf and pTRXFUS respectively.

lane 1: standard protein marker;
   lane 2: supernatant of disrupted *E. coli*/pTRXFUS-GMcsf transformant induced for the protein expression;
   lane 3: precipitate of disrupted *E. coli*/pTRXFUS-GMcsf transformant induced;
   lane 4: supernatant of disrupted *E. coli*/pTRXFUS transformant induced;
   lane 5: precipitate of disrupted *E. coli*/pTRXFUS transformant induced;

FIG. 8 depicts a strategy for constructing the *E. coli* expression vector pLysN-Gcsf which expresses Gcsf protein by using the expression vector pGE-lysN.

Figure 9:
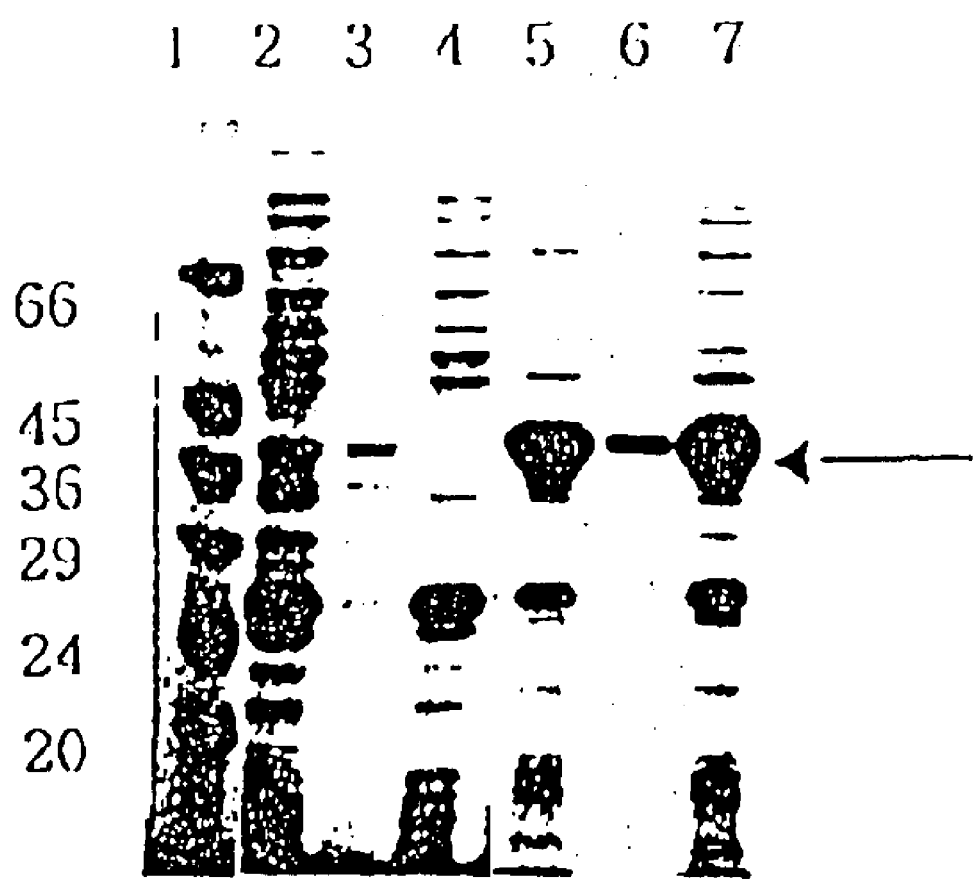
Figure 10:
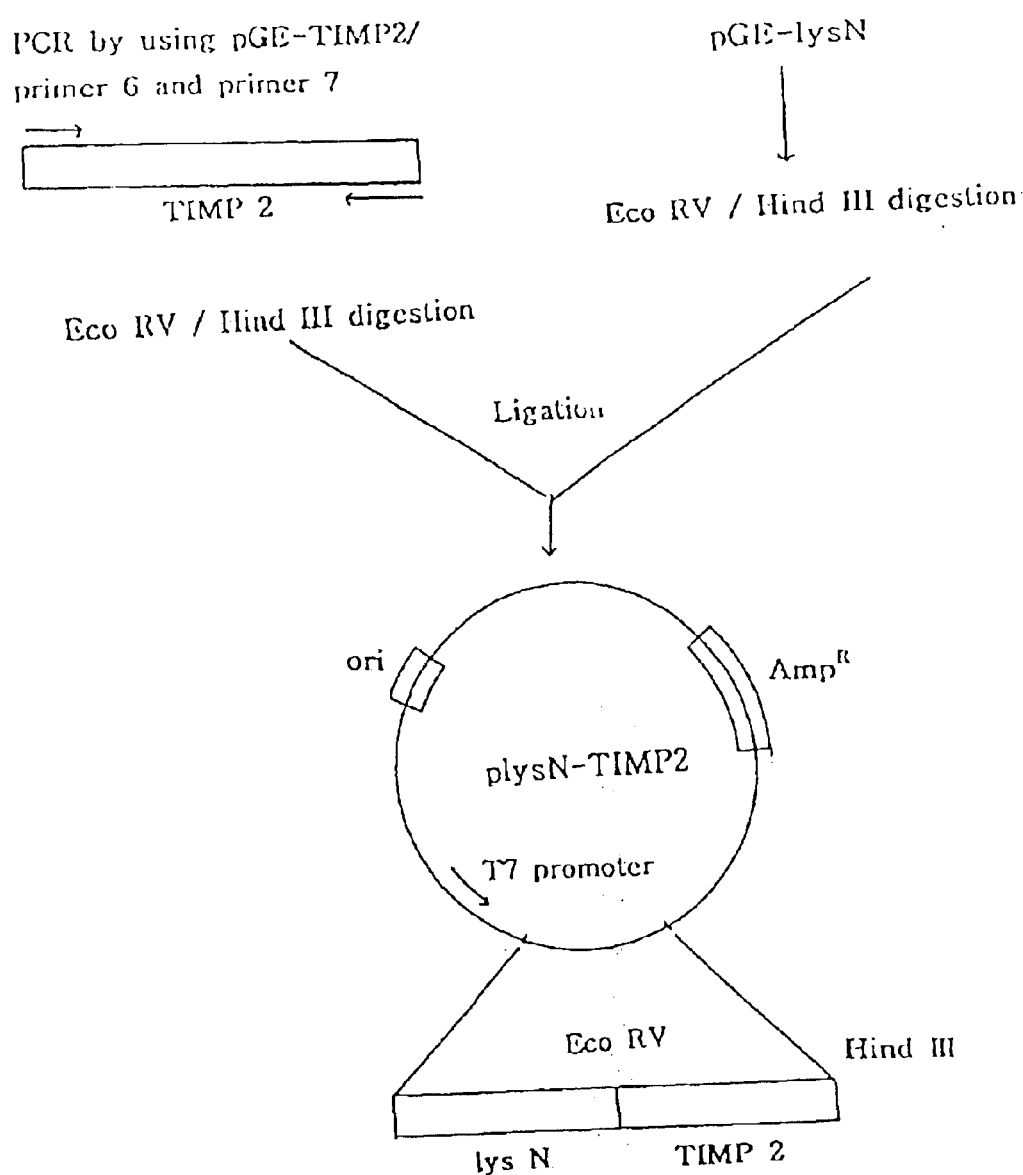

FIG. 9 depicts the expression of Gcsf protein by performing SDS-polyacrylamide gel electrophoresis, which used *E. coli* HMS 174 strain transformed with the expression vector pLysN-Gcsf.

lane 1: standard protein marker;
   lane 2: total proteins of *E. coli* transformant;
   lane 3: precipitate of *E. coli* transformant;
   lane 4: supernatant of *E. coli* transformant;
   lane 5: total proteins of *E. coli* transformant induced for the protein expression;
   lane 6: precipitate of disrupted *E. coli* transformant induced;
   lane 7: supernatant of disrupted *E. coli* transformant induced FIG. 10 depicts a strategy for constructing the *E. coli* expression vector pLysN-TIMP2 which expresses TIMP2 protein by using the expression vector pGE-lysN.

Figure 11:

FIG. 11 depicts the expression of TIMP2 protein by performing SDS-polyacrylamide gel electrophoresis, which used *E. coli* HMS 174 strain transformed with the expression vector pLysN-TIMP2.

lane 1: standard protein marker;
   lane 2: total proteins of *E. coli*/pGE-lysN transformant;
   lane 3: total proteins of *E. coli*/pGE-lysN transformant induced for the protein expression;
   lane 4: precipitate of disrupted *E. coli*/pGE-lysN transformant induced;
   lane 5: supernatant of disrupted *E. coli*/pGE-lysN transformant induced;
   lane 6: total proteins of *E. coli* transformant
   lane 7: total proteins of *E. coli* transformant induced;
   lane 8: precipitate of disrupted *E. coli* transformant induced;
   lane 9: supernatant of disrupted *E. coli* transformant induced

DESCRIPTION OF THE PREFERRED EMBODIMENTS

The present invention provides expression vectors which produce useful foreign proteins as soluble forms by exploiting the structural characteristics of aminoacyl-tRNA synthetase. All kinds of aminoacyl-tRNA synthetase genes can be used to prepare expression vectors of the present invention as fusion partner proteins.

The present invention provides expression vectors which use lysyl-tRNA synthetase (Lys RS) which has been studied well as a fusion partner. At that time, Lys RS protein gene can be selected among lys S gene and lys U gene.

Lys RS protein gene can be obtained by performing polymerase chain reaction (PCR) which utilized *E. coli* chromosomal DNA as a template.

Particularly, lys S gene obtained by the above process has been inserted into the plasmid vector such as pGEMEX™-1 (Promega) so as to construct the expression vector pGE-lysRS of the present invention (see FIG. 2). *E. coli* strains proper for the expression have been transformed with the expression vector pGE-lys RS and induced to express Lys RS protein. As a result, Lys RS protein was expressed well, to 80% of total soluble proteins of the host cell. Generally *E. coli* transformants are cultured at 37° C. in order to express Lys RS protein of the present invention. But soluble proteins are expressed efficiently at low temperature such as 15° C.–30° C. which facilitates the increase of the soluble protein ratio.

The present invention provides expression vectors which uses the N-terminal domain of Lys RS protein as a fusion partner protein.

In order to produce useful foreign proteins effectively, the expression vector of the present invention contains linker peptide sequence, tag sequence, protease recognition site, restriction enzyme recognition site and so forth selectively, in addition to the N-terminal domain of Lys RS protein. Therefore, fusion proteins expressed by using the expression vectors can be produced as forms of soluble proteins in the host cells and separated easily and only the foreign proteins can be purified by digesting the fusion proteins with specific protease.

Particularly, the N-terminal domain gene of Lys RS protein can be obtained by performing polymerase chain reaction which utilizes the expression vector pGE-lysRS as a template. And the N-terminal domain gene obtained by the above process has been inserted into the plasmid vector pGEMEX™-ΔNdeI to construct the expression vector pGE-lys N of the present invention (see FIG. 4).

The *E. coli* HMS 174 strain was transformed by the expresseion vector pGE-lysN of the present invention and the transformant has been deposited with Korea Research Institute of Bioscience and Biotechnology, Korea, on Sep. 26, 1997 (accession number: KCTC 0388 BP).

The expression vector constructed by the above process has the following characteristics. The expression vector of the present invention contains T7 promoter which regulates transcription of the fusion protein. In addition to T7 promoter, all kinds of promoters which can be used in *E. coli* strans, such as tac promoter, λ pL promoter and the like, is available for the expression vector of the present invention.

The expression vectors of the present invention have been constructed in order to exploit the N-terminal domain of Lys RS protein as a fusion partner protein effectively.

In the N-terminal domain of Lys RS protein, helix 1 structure exists. Since the helix 1 structure is very close to linker peptide, it may prevent enteropeptidase from digesting fusion protein and affect protein folding. In order to provide the suitable expression vector for the production of foreign proteins, helix 1 structure can be removed from the expression vector.

The present invention provides the expression vector removed at the helix 1 structure to prepare foreign proteins more efficiently.

Preferably, the expression vector of the present invention contains the N-terminal domain of Lys RS protein which is deleted at the amino acid residues 1 to 13. Preferably the expression vector also contains the N-terminal domain of LysRS protein which is deleted at the amino acid residues 1 to 29.

In addition, preferably the expression vector of the present invention contains OB fold gene which is involved in folding process of Lys RS protein. Particularly, the expression vector contains the N-terminal domain of Lys RS protein which is deleted at the amino acid residues 1 to 65 corresponding to helix structure 1, 2 and 3. The expression vectors above are suitable for the production of fusion proteins as soluble forms.

The expression vector of the present invention can also contain OB fold domain gene of other proteins in addition to the N-terminal domain gene of Lys RS protein. In detail, OB fold genes found in aspartyl-tRNA synthetase of yeast, B subunit of thermolabile enterotoxin, berotoxin and Staphylococcal nuclease can be utilized for the construction of the expression vector.

The expression vector of the present invention contains linker peptide connecting fusion partner protein and foreign protein. Particularly, the amino acid residues 147 to 154 of Lys RS protein is used as a linker peptide. This linker peptide is very useful since it is protruded on the protein surface and the length of linker peptide can be controlled according to the foreign proteins expressed. The expression vector can also contain useful linker peptides of other proteins in addition to Lys S protein described above.

The expression vector of the present invention also contains histidine tag of 6 histidine residues after the above linker peptide. This histidine tag enables the fusion proteins expressed with the expression vector to be purified easily. Practically, histidine tagged fusion protein can be separated and purified easily by using nickel chelating column chromatography and the like.

In addition to hisitidine tag, polyarginine or consensus biotinylation sequence can be inserted into the expression vector. Fusion proteins produced by using the above expression vector can be separated and purified from various affinity column chromatographies. The tag sequences described above can be located in any available region of C-terminus or N-terminus of the fusion protein.

The expression vector of the present invention contains protease recognition site in order to separate only foreign protein from the expressed and purified fusion protein. In detail, the expression vector of the present invention contains enteropeptidase recognition site (DDDDK sequence: SEQ ID NO: 10) after 6 histidine residues, which enables the fusion protein to be easily separated into fusion partner protein and foreign protein. At that time, enteropeptidase digests the C-terminus of the above enteropeptidase recognition site.

In addition, the above protease recognition site can be substituted with a thrombin recognition site (LVPRGS sequence; SEQ ID NO: 11) or with an Xa factor recognition site (IEGR sequence: SEQ ID NO: 12), in order to efficiently produce foreign proteins.

The expression vector of the present invention contains restriction enzyme sites after the above protease recognition site, in order to insert foreign protein genes conveniently. In detail, the expression vector pGElysN of the present invention contains restriction enzyme recognition sites KpnI-BamHI-EcoRi-SalI-HindIII. In addition to the above recognition sites, all kinds of restriction recognition sites that are conveniently used in cloning foreign genes can be inserted.

Various foreign proteins which are expressed as inclusion bodies in *E. coli* can be prepared as soluble forms efficiently by using the expression vectors of the present invention.

Particularly, the present invention provides the expression vectors which uses the N-terminal domain of lysyl-tRNA synthetase (Lys N) in order to produce human granulocyte and macrophage colony stimulating factor (GMcsf), human granulocyte colony stimulating factor (Gcsf) and human tissue inhibitor of metalloprotease (TIMP 2) and the like massively.

The present invention constructs the expression vector which produces GMcsf protein as a soluble form by using Lys N protein. In detail, GMcsf gene was obtained by performing polymerase chain reaction which utilized the expression vector pTRXFUS-GMcsf as a template. And the GMcsf gene obtained above has been inserted into the expression vector pGE-lysN to construct the expression vector plysN-GMcsf of the present invention (see FIG. 5).

In order to examine the availability of Lys N as a fusion partner protein, GMcsf protein fused with Lys N protein has been compared with GMcsf protein fused with thioredoxin according to their expression. For the previous comparison, the expression vector pTRXFUS-GMcsf which contains GMcsf gene and thioredoxin gene and produces their fusion protein has been constructed (see FIG. 7).

In addition, the present invention constructs the expression vector which produces Gcsf protein as a soluble form. In detail, Gcsf gene was obtained by performing polymerase chain reaction which utilized the expression vector pTRXFUS-Gcsf as a template. And the Gcsf gene has been inserted into the expression vector pGE-lysN to construct the expression vector plysN-Gcsf of the present invention (see FIG. 8).

In addition, the present invention constructs the expression vector which produces TIMP 2 protein as a soluble protein. In detail, TIMP 2 gene was obtained by performing polymerase chain reaction which utilized the vecor pGET-IMP 2 as a template. And the TIMP 2 gene has been inserted into the expression vector pGE-lys N to construct the expression vector pGElysN-TIMP 2 of the present invention (see FIG. 10).

The *E. coli* strains proper for the expression have been transformed with the above expression vectors. Transformants have been cultured at 37° C. and as results foreign proteins fused with Lys N protien, namely, Lys N-GMcsf protein, Lys N-Gcsf protein and Lys N-TIMP 2 protein as soluble forms were expressed at the ratio of 5–30% of total soluble proteins (see FIG. 6, FIG. 9 and FIG. 11). On the other hand, when thioredoxin was used as a fusion partner protein, fusion protein was expressed as an inclusion body (see FIG. 7). Therefore, Lys N protein of the present invention is identified to be a more outstanding fusion partner protein than thioredoxin.

Practical and presently preferred embodiments of the present invention are illustrative as shown in the following Examples.

However, it will be appreciated that those skilled in the art, on consideration of this disclosure, may make modification and improvements within the spirit and scope of the present invention.

EXAMPLES

Example 1

Cloning of lys S Gene and Construction of the Expression Vector pGE-lysRS

In order to clone lys S gene which is necessary to construct the expression vector of the present invention, polymerase chain reaction (PCR) was performed, which utilized primer 1 of SEQ ID. NO: 1, primer 2 of SEQ ID. NO: 2 and E. coli chromosomal DNA as a template (see Sequence Listing). Amplified lys S gene was digested with resctriction enzyme NdeI and HindIII.

For the convenience of cloning process, among two NdeI sites of plasmid PGEMEX™-1 (Promega) NdeI site located on DNA sequence 3251 was removed from the plasmid as shown in FIG. 2 to construct the plasmid pGEMEX™-ΔNdel. The plasmid pGEMEX™-ΔNdeI was digested with restriction enzyme NdeI and HindIII. The plasmid and PCR product digested above were electrophoresed on 1% agarose gel and the gel which contained the DNA fractions appearing at long wavelenth of UV was cut. Each DNA fraction was eluted from the gel by Jetsorb Kit (GENOMED) and was ligated.

As a result, the expression vector pGE-lysRS containing lys S gene was constructed.

Example 2

Expression of Lys S Protein

E. coli HMS 174 strain was transformed with the expression vector pGE-lysRS constructed in Example 1. The E. coli transformant selected was inoculated into 1.5 ml of LB medium containing ampicillin 100 μg/ml, chloramphenicol 30 μg/ml. The transformant was cultured overnight at 37° C., and the growing culture was again inoculated into 50 ml of LB media. When the concentration of E. coli was 0.5 at $OD_{600}$, IPTG was added into the E. coli culture in order to induce the expression of protein and again the E. coli culture was incubated for more 5 hours. The above culture broth was centrifuged for 10 minutes at 5,000 g, and cell pellet was suspended in 10 ml of phosphate buffered saline (PBS) buffer. The cells were disrupted and the crude exrtact prepared in the above process was centrifuged for 15 minutes at 15,000 g in order to separate supernatant from precipitate. This precipitate was again suspended in 10 ml of PBS buffer. 28 μl of above each sample was mixed with 7 μl of 5×SDS loading buffer, and boiled for 5 minutes. 10 μl of the above mixture was loaded onto 12% SDS-polyacrylamide gel, electrophoresed at 120 V and identified with the protein band by using Coomasie blue dye.

As a result, as is shown in lane 7 of FIG. 3, the expression vector of the present invention expresses Lys S protein highly at the ratio of 80% of total soluble proteins (see FIG. 3).

Example 3

Construction of the Expression Vector pGE-lysN

In order to construct the expression vector using the N-terminal domain of Lys S protein as a fusion partner protein, polymerase chain reaction was performed, which utilized primer 1 of SEQ ID. NO: 1, primer 3 of SEQ ID. NO: 3 and the expression vector pGE-lysRS constructed in Example 1 as a template (see Sequence Listing).

Amplified gene in the above reaction was digested with restriction enzyme NdeI and HindIII and the plasmid vector pGEMEX™-ΔNdel was also digested with NdeI and HindIII. And above products were ligated after elution (see FIG. 4).

As a result, the expression vector containing the N-terminal domain gene of Lys S protein was constructed and named as the expression vector pGE-lysN (accession number: KCTC 0388 BP).

Example 4

Construction of the Expression Vector plysN-GMcsf and Expression of Fusion Protein LysN-GMcsf In order to express human GMcsf protein as a soluble protein in E. coli, which has been expressed independently as an inclusion body in E. coli, GMcsf gene was cloned into the expression vector pGE-lysN of the present invention (see FIG. 5).

In order to obtain GMcsf gene, PCR was performed by utilizing primer 4 of SEQ ID. NO: 4, primer 5 of SEQ ID. NO: 5 and the expression vector pTRXFUS-GMcsf as a template (see Sequence Listing).

Amplified gene by the above reaction was digested with restriction enzyme KpnI and HindIII and the expression vector pGE-lysN of the present invention was also digested with KpnI and HindIII. And the above products were ligated after elution. As a result, the expression vector which produces GMcsf protein fused with LysN protein was constructed and named as the expression vector plysN-GMcsf.

In addition, E. coli was transformed with the expression vector plysN-GMcsf. As a result, fusion protein was expressed as is shown in FIG. 6 and the size is 33 kDa as is predicted. In addition, most LysN-GMcsf fusion protein was expressed highly at the ratio of 10% of total soluble proteins (see FIG. 6).

Example 5

Construction of the Expression Vector pTRXFUS-GMcsf and Expression of Thioredoxin-GMcsf In order to examine the availability of Lys N of the present invention as a fusion partner protein, as a control experiment the effect of fusion partner protein, thioredoxin on the expression of GMcsf fusion protein was examined.

The expression vector pTRXFUS-GMcsf which expresses GMcsf fusion protein was constructed by subcloning GMcsf gene into KpnI and BamHI site of the expression vector pTRXFUS using thioredoxin as a fusion partner protein (see FIG. 7).

When the *E. coli* transformed with the expression vector of the present invention was cultured at 37° C., fusion proteins were expressed as inclusion bodies (see FIG. 7, lane 3).

As a result, thioredoxin was less effective than Lys N protein as a fusion partner protein.

Example 6

Construction of the Expression Vector plysN-Gcsf and Expression of LysN-Gcsf Fusion Protein In order to express human Gcsf (granulocyte colony stimulating factor) as a soluble protein, which has been expressed as an inclusion body independently in *E. coli*, Gcsf gene was cloned by performing the same method as Example 4.

Polymerase chain reaction was performed by utilizing primer 6 of SEQ ID. NO: 6, primer 7 of SEQ ID. NO: 7 and the plasmid vector pTRXFUS-Gcsf as a template (see Sequence Listing). Gcsf gene amplified by the above reaction was phosphorylated by T4 polynucleotide kinase, and the expression vector pGE-lysN was also digested with EcoRV, and then treated by CIP (calf intestine phosphatase). The two resultants were ligated after elution by performing the same method of Example 1. As a result, the expression vector plysN-Gcsf was constructed which expresses Gcsf-LysN fusion protein (see FIG. 8).

In addition, fusion protein was expressed by transforming *E. coli* with the expression vector plysN-Gcsf. As a result, fusion protein was expressed as is shown in FIG. 9, and the size of protein is 36 kDa as is predicted. Particularly, Lys-Gcsf fusion protein was expressed as a soluble protein, and occupied 30% of total soluble proteins.

Example 7

Construction of the Expression Vector plysN-TIMP2 and Expression of Fusion Protein LysN-TIMP2

In order to express human TIMP2 (tissue inhibitor of metalloprotease 2) as a soluble protein, which has been expressed as an inclusion body in *E.coli*, TIMP2 gene was inserted into the expression vector pGE-lysN of the present invention.

In order to clone TIMP2 gene, polymerase chain reaction was performed by utilizing primer 8 of SEQ ID. NO: 8, primer 9 of SEQ ID. NO: 9 and the plasmid vector pGE-TIMP2 (see Sequence Listing). Amplified TIMP2 gene by the above reaction was digested with restriction enzyme EcoRV and HindIII, and the expression vector pGE-lysN of the present invention was also digested by EcoRV and HindIII. Above two resultants were ligated after elution by performing the same method as Example 1. As a result, the expresion vector plysN-TIMP2 which expresses fusion protein LysN-TIMP2 was constructed (see FIG. 10).

In addition, fusion protein was expressed by transforming *E. coli* with the expression vector plysN-TIMP2. As a result, fusion protein was expressed as is shown in FIG. 11, and the size of protein is 41 kDa as is predicted. Particularly, Lys N-TIMP2 fusion protein was expressed as a soluble protein, to 5% of total soluble proteins (see FIG. 11, lane 9).

The expression vectors of the present invention expresses lysyl-tRNA synthetase and foreign proteins fused with the N-terminal domain of lysyl-tRNA synthetase as soluble forms, which makes their protein activities maintained. Thus the present invention is outstanding in view of recombinant DNA technology.

Practically, the expression vector of the present invention expresses Lys RS protein highly at the ratio of 80% of total soluble proteins, and also expresses foreign proteins fused with Lys N protein highly at the ratio of 5–30%. In addition, Lys N protein is more effective than thioredoxin developed already.

Particularly, the expression vectors of the present invention can produce foreign protein efficiently, for example GMcsf, Gcsf and TIMP2 proteins. In addition to the previous proteins, the expression vector of the present invention is useful to produce foreign proteins which are difficult or impossible to be obtained as active forms and have high molecular weights, such as antibodies, tissue plasminogen activator and factor VIII.

In addition, the expression vector of the present invention is constructed to make foreign proteins genes inserted, fusion proteins purified easily and protease recognition site digested specifically, which facilitates the production of intact target proteins. Thus the expression vector is very useful to produce various foreign proteins.

What is claimed is:

1. A method for producing foreign proteins as soluble forms by using an N-terminal domain of an *Escherichia coli* lysS lysyl-tRNA synthetase as a fusion partner, comprising the steps of:
   a) transforming *Escherichia coli* with an expression vector that comprises
      (i) a polynucleotide sequence encoding said N-terminal domain of an *Escherichia coli* lysS lysyl-tRNA synthetase that is obtained by amplification of *Escherichia coli* genomic DNA using a pair of primers, wherein the primers have the structure of SEQ ID NO: 1 and SEQ ID NO:3, respectively, and
      (ii) a polynucleotide sequence encoding a protease recognition site, and a polynucleotide sequence encoding a foreign protein inserted in a polynucleotide sequence encoding a restriction enzyme recognition site, in due order;
   b) producing a fusion protein by culturing the transformant;
   c) recovering said fused protein from the culture; and
   d) cleaving said fusion protein with a protease.

2. The method according to claim 1, wherein the expression vector further comprises a DNA sequence encoding a tag sequence, wherein the DNA sequence encoding the linker peptide or the tag protein, is positioned between the DNA sequence encoding the N-terminal domain of an *Escherichia coli* lysS lysyl-tRNA synthetase, and the DNA sequence encoding a protease recognition site.

3. The method according to claim 1, wherein the expression vector is pGE-lysN.

4. The method according to claim 1, wherein the transformant KCTC-00388BP.

5. The method according to claim 1, wherein the foreign protein is human granulocyte colony stimulating factor protein.

6. The method according to claim 1, wherein the foreign protein is human tissue inhibitor of metalloprotease protein.

7. The method according to claim 1, wherein the protease recognition site is a DDDDK enteropeptidase recognition site of SEQ ID NO: 10, a LVPRGS thrombin recognition site of SEQ ID NO: 11, or an IEGR Xa factor recognition site of SEQ ID NO: 12.

8. The method according to claim 2, wherein the DNA sequence encoding a tag protein is selected from the group consisting of, a DNA sequence encoding a 6 residue histidine tag, a DNA sequence encoding polyarginine, and a consensus biotinylation sequence.

9. The method of claim 1, wherein the fusion partner is located 5' of the DNA sequence encoding a foreign protein.

* * * * *

SEQUENCE LISTING

<160> NUMBER OF SEQ ID NOS: 12

<210> SEQ ID NO 1
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 1
gactaccata tgtctgaaca acacgcacag ggcgct          36

<210> SEQ ID NO 2
<211> LENGTH: 42
<212> TYPE: DNA
<213> ORGANISM: Artificial Sequence

```
<220> FEATURE:
<223> OTHER INFORMATION: Description of Artificial Sequence: Primer

<400> SEQUENCE: 2
gactacaagc ttctattatt ttaccggacg catcgccggg aa                          42

<210> SEQ ID NO 3
<211> LENGTH: 96
<212> TYPE: DNA
<213> ORGANISM: Artificial Sequence
<220> FEATURE:
<223> OTHER INFORMATION: Description of Artificial Sequence: Primer

<400> SEQUENCE: 3
gactacaagc ttgtcgacga tatcggatcc ggtacccttg tcatcgtcat cgtggtggtg       60
gtggtggtgc ggcagcggac gcagtgcttt ggtcag                                 96

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 4
gacaagggta ccgcaccccg ctcgcccagc ccc                                    33

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 5
gagcgcaagc tttcactcct ggactggctc ccagca                                 36

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 6
gacaagggta ccacccccct gggccctgcc agc                                    33

<210> SEQ ID NO 7
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 7
gacaagaagc tttcatcagg gctgggcaag gtggcg                                 36

<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence: Primer
```

-continued

```
<400> SEQUENCE: 8
gtcatcgata tctgcagctg ctccccggtg cac                                    33

<210> SEQ ID NO 9
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 9
gtcatcaagc tttcattatg ggtcctcgat gtcgag                                 36

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 10

Asp Asp Asp Asp Lys
1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 11

Leu Val Pro Arg Gly Ser
1               5

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 12

Ile Glu Gly Arg
1
```